US010586997B1

(12) United States Patent
Ingersoll et al.

(10) Patent No.: US 10,586,997 B1
(45) Date of Patent: Mar. 10, 2020

(54) AQUEOUS NA-ION REDOX FLOW BATTERY WITH CERAMIC NASICON MEMBRANE

(71) Applicant: National Technology & Engineering Solutions of Sandia, LLC, Albuquerque, NM (US)

(72) Inventors: David Ingersoll, Albuquerque, NM (US); Ganesan Nagasubramanian, Albuquerque, NM (US); Eric Allcorn, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 156 days.

(21) Appl. No.: 15/709,653

(22) Filed: Sep. 20, 2017

Related U.S. Application Data

(60) Provisional application No. 62/397,664, filed on Sep. 21, 2016.

(51) Int. Cl.
| | | |
|---|---|---|
| *H01M 8/18* | (2006.01) | |
| *H01M 8/20* | (2006.01) | |
| *H01M 4/90* | (2006.01) | |
| *C07C 39/08* | (2006.01) | |
| *C07C 229/16* | (2006.01) | |
| *C07D 221/06* | (2006.01) | |

(52) U.S. Cl.
CPC .............. *H01M 8/188* (2013.01); *C07C 39/08* (2013.01); *C07C 229/16* (2013.01); *C07D 221/06* (2013.01); *H01M 4/9008* (2013.01); *H01M 4/9066* (2013.01)

(58) Field of Classification Search
CPC ........ Y02E 60/528; H01M 8/188; H01M 8/20
See application file for complete search history.

(56) References Cited

U.S. PATENT DOCUMENTS

| | | | |
|---|---|---|---|
| 8,722,227 B2 | 5/2014 | Chiang et al. | |
| 8,753,761 B2 | 6/2014 | Esswein et al. | |
| 2009/0005824 A1* | 1/2009 | Visco .................. | A61N 1/0436 607/3 |
| 2009/0253024 A1* | 10/2009 | Buttry .................. | H01M 4/137 429/492 |
| 2010/0068629 A1* | 3/2010 | Gordon .................. | H01M 4/06 429/325 |
| 2010/0185036 A1* | 7/2010 | Morimoto ............. | C02F 1/4693 588/20 |
| 2013/0084474 A1* | 4/2013 | Mills .................. | H01M 4/9016 429/9 |

(Continued)

*Primary Examiner* — Imran Akram
(74) *Attorney, Agent, or Firm* — Medley, Behrens & Lewis, LLC; Samantha Updegraff

(57) ABSTRACT

A redox flow battery is described herein that has a sodium-super-ionic-conductor NaSICON barrier disposed between an anolyte chamber of the battery and the catholyte chamber of the battery. The NaSICON barrier prevents crossover of solvents or active redox species between the anolyte chamber and the catholyte chamber, while permitting transport of sodium ions between the chambers. In exemplary embodiments, the anolyte chamber includes an anolyte solution that comprises a first active redox species dissolved in a first solvent, while the catholyte chamber includes a catholyte solution that comprises a second active redox species dissolved in a second solvent.

16 Claims, 2 Drawing Sheets

(56) References Cited

U.S. PATENT DOCUMENTS

| | | | |
|---|---|---|---|
| 2013/0130085 A1* | 5/2013 | Choi | H01M 4/364 |
| | | | 429/105 |
| 2013/0224632 A1* | 8/2013 | Roumi | H01M 2/166 |
| | | | 429/516 |
| 2013/0344367 A1* | 12/2013 | Chiang | H01M 8/188 |
| | | | 429/101 |
| 2014/0178735 A1 | 6/2014 | Wang et al. | |
| 2016/0126581 A1 | 5/2016 | Timofeeva et al. | |
| 2016/0149211 A1* | 5/2016 | Hart | H01M 4/38 |
| | | | 429/103 |
| 2016/0226118 A1 | 8/2016 | Shaw et al. | |
| 2017/0309943 A1* | 10/2017 | Angell | H01M 8/188 |

* cited by examiner

AQUEOUS NA-ION REDOX FLOW BATTERY WITH CERAMIC NASICON MEMBRANE

RELATED APPLICATION

This Application claims priority to U.S. Provisional Patent Application No. 62/397,664, filed on Sep. 21, 2016, and entitled "Aqueous Na-Ion Redox Flow Battery with Ceramic NaSICON Membrane", the entirety of which is incorporated herein by reference.

STATEMENT OF GOVERNMENTAL INTEREST

This invention was made with Government support under Contract No. DE-NA0003525 awarded by the United States Department of Energy/National Nuclear Security Administration. The U.S. Government has certain rights in the invention.

BACKGROUND

Redox flow batteries (RFBs) find application in various operational environments in which high-capacity energy storage is required. Conventional RFBs generally employ ion permeable membranes in order to separate anolyte and catholyte active redox species while retaining sufficient ionic conductivity to allow charge-compensating ions to permeate across the membrane. However, in addition to allowing transport of charge-compensating ions, these conventional membranes are in many cases permeable to the anolyte and catholyte active redox species and/or the solvents in which these species are dissolved. Over time, this crossover mixing of the catholyte and anolyte active species and their solvents degrades the RFB's performance and energy capacity. Furthermore, certain combinations of anolyte/catholyte active redox species or anolyte/catholyte solvents are impractical or impossible to achieve, as these materials may exhibit undesirable or hazardous chemical reactions with one another as a result of crossover mixing.

Crossover of redox active species and solvents can be partially alleviated by using solid state ionic conducting materials such as Lithium super-ionic-conductor (LiSICON) and $\beta''$-alumina to separate the cathode and anode portions of the RFB. However, these materials are poorly suited to use in RFBs. LiSICON exhibits relatively low ionic conductivity at room temperature (e.g., on the order of $10^{-6}$ S/cm). $\beta''$-alumina has low room temperature conductivity, and degrades quickly in the presence of water, thereby necessitating the use of organic solvents that are poor conductors, are expensive, and raise various safety concerns.

SUMMARY

The following is a brief summary of subject matter that is described in greater detail herein. This summary is not intended to be limiting as to the scope of the claims.

Various technologies pertaining to an RFB with a solid-state ion-conducting membrane are described herein. The RFB comprises one or more cells, each cell comprising a cathode portion and an anode portion. The cathode and anode portions of each cell comprise respective solvents with an active redox species dissolved or suspended therein. In an embodiment, the active redox species of the cathode portion is a different active redox species from the active redox species of the anode portion. In a further embodiment, the solvent of the cathode portion is a different solvent from the solvent of the anode portion. The anode portion and cathode portion further comprise an electrolyte dissolved in their respective solvents.

The RFB further comprises a barrier that is made up of a material comprising a sodium super-ionic-conductor (NaSICON). The barrier separates the anode portion from the cathode portion of the RFB such that the solvents and the active redox species of the RFB do not migrate from the cathode portion to the anode portion or from the anode portion to the cathode portion. In a discharge cycle, an electrical load is connected between the anode portion and the cathode portion, and the redox active species of the anode portion is oxidized. Free electrons flow from the anode portion of the RFB to the cathode portion of the RFB, resulting in a current that flows through the load. The free electrons reduce the redox active species of the cathode portion.

When electrons flow from the anode portion to the cathode, positive sodium ions, $Na^+$, migrate across the NaSICON barrier that separates the anode portion from the cathode portion. The NaSICON barrier is highly permeselective, such that the $Na^+$ ions readily migrate across the NaSICON barrier to balance the flow of electrons while there is substantially no crossover of solvent or active redox species between the anode portion and the cathode portion of the RFB. The NaSICON barrier is a solid barrier that is substantially nonporous.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
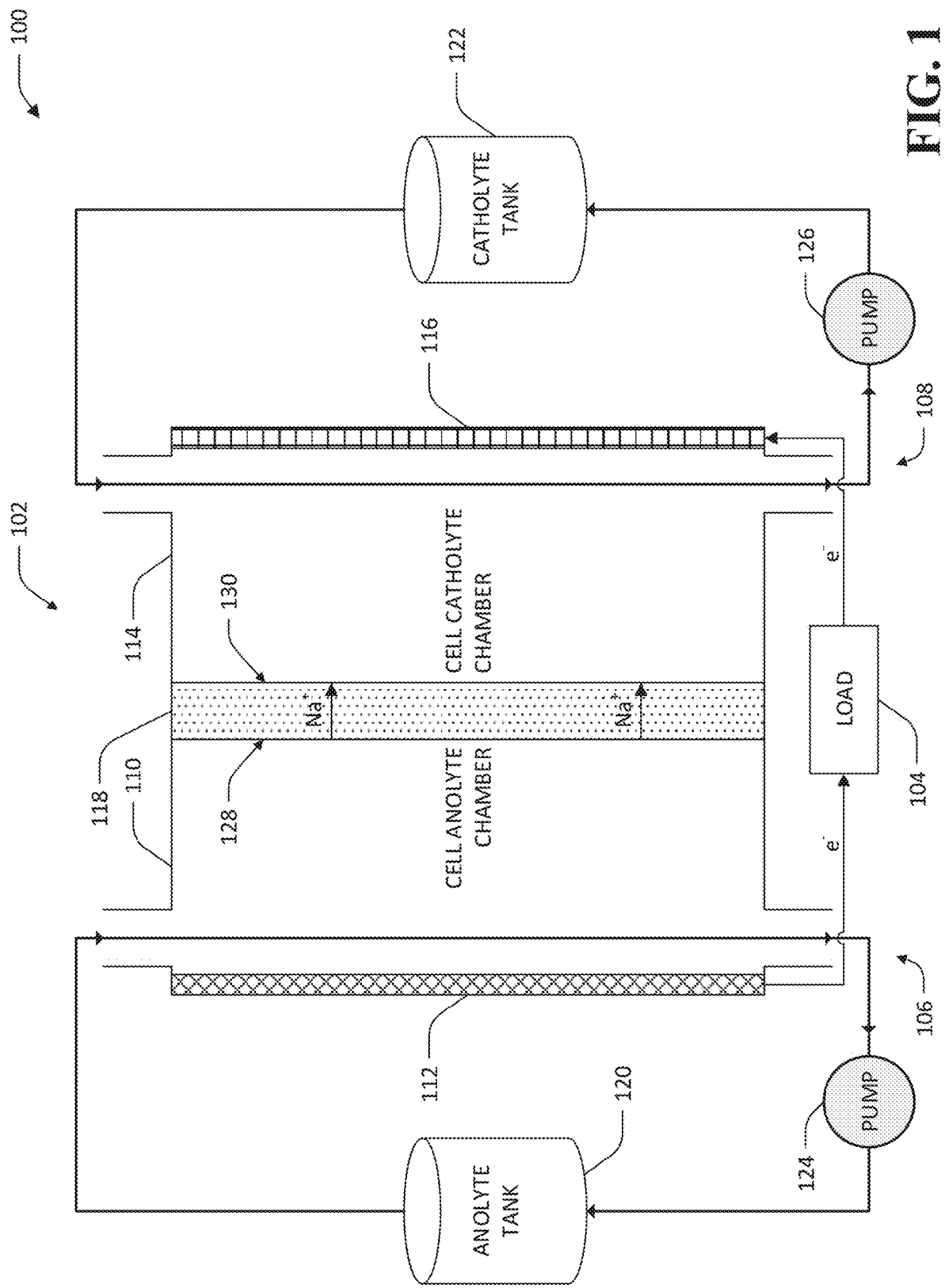
FIG. 1 is a diagram of an exemplary redox flow battery system.

Various technologies pertaining to a redox flow battery are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

It is also to be understood that a component or system may be localized on a single device or distributed across several devices. Additionally, as used herein, the term "exemplary" is intended to mean serving as an illustration or example of something, and is not intended to indicate a preference.

With reference to FIG. 1, an exemplary redox flow battery (RFB) system 100 is illustrated in a discharge mode of operation. The system 100 includes a cell 102 that drives an electrical load 104. The cell 102 comprises an anode portion 106 (anode) and a cathode portion 108 (cathode) between which the load 104 is connected. The anode 106 comprises an anolyte chamber 110 and an anode electrode 112 that is coupled to the anolyte chamber 110. Similarly, the cathode 108 comprises a catholyte chamber 114 and a cathode electrode 116 that is coupled to the catholyte chamber 114. The anolyte chamber 110 and catholyte chamber 114 comprise vessels suited for containment of various fluids that comprise anolyte and catholyte solutions, as discussed in greater detail below. In some embodiments, the anode electrode 112 and cathode electrode 116 of the cell 102 form external walls of the anolyte chamber 110 and catholyte chamber 114, respectively. Such embodiments facilitate use of the cell 102 in multi-cell battery configurations, such as discussed in greater detail below with respect to FIG. 2.

The cell 102 further comprises a barrier 118 that comprises a sodium-super-ionic-conductor (NaSICON) (e.g., a compound having a chemical formula of $Na_{1+x}Zr_2Si_xP_{3-x}O_{12}$, where $0<x<3$). The barrier 118 separates the anolyte chamber 110 from the catholyte chamber 114. The system 100 further comprises an anolyte tank 120 that is coupled to the anolyte chamber 110 such that fluid can be transported from the anolyte tank 120 to the anolyte chamber 110 and vice versa. Similarly, the system 100 comprises a catholyte tank 122 that is coupled to the catholyte chamber 114 such that fluid can be transported from the catholyte tank 122 to the catholyte chamber 114 and from the catholyte chamber 114 to the catholyte tank 122. The system 100 can further include a first pump 124 that facilitates fluid flow between the anolyte tank 120 and anolyte chamber 110, and a second pump 126 that facilitates fluid flow between the catholyte tank 122 and the catholyte chamber 114. It is to be understood that in addition to or in place of the pumps 124, 126, embodiments consistent with the disclosure provided herein may incorporate a gravity feed, additional pumps, etc. in order to facilitate fluid flow between the anolyte chamber 110 and anolyte tank 120 or the catholyte chamber 114 and the catholyte tank 122.

The anolyte chamber 110 and the anolyte tank 120 each contain an anolyte solution of an active redox species dissolved in a solvent, wherein an active redox species is a chemical species that participates in redox reactions that occur in operation of the RFB system 100. Similarly, the catholyte chamber 114 and the catholyte tank 122 each contain a catholyte solution of an active redox species dissolved in a solvent. The solution in the anolyte chamber 110 and the anolyte tank 120 further comprises a sodium compound dissolved in the solvent. For example, the anolyte solution can comprise a sodium salt such as sodium chloride, sodium phosphate, sodium bromide, sodium sulfate, etc. In additional embodiments, the catholyte chamber 114 and the catholyte tank 122 comprises the same or a different sodium ionic compound as the anolyte chamber 110 and the anolyte tank 120. The anolyte active redox species and the catholyte active redox species are selected to facilitate redox reactions wherein one of the anolyte active redox species or the catholyte active redox species is reduced and the other is oxidized.

In a discharge mode of operation of the RFB system 100, electrons flow from the anode electrode 112 to the cathode electrode 116 through the load 104 when the load 104 is connected between the electrodes 112, 116. The anolyte active redox species is oxidized and the catholyte active species is reduced as electrons flow from the anolyte chamber 110 by way of the anode electrode 112 to the catholyte chamber 114 by way of the cathode electrode 116. As electrons flow from the anolyte chamber 110 to the catholyte chamber 114 through the load 104, positive sodium ions, $Na^+$, migrate across the NaSICON barrier 118 to balance the flow of electrons and maintain charge neutrality of the anolyte chamber 110 and the catholyte chamber 114. A magnitude of the current of electrons flowing through the load 104 depends in part upon a voltage of the cell 102 and an electrical resistance of the load 104, where the voltage of the cell 102 is the voltage between the anode electrode 112 of the cell 102 and the cathode electrode 116 of the cell 102. Electrical characteristics of the cell are further affected by parameters such as concentration of active redox species in the anolyte and catholyte solutions, state of charge of the active redox species, diffusion of the active redox species, and reaction kinetics of the active redox species. In turn, some of these parameters may be affected by operating parameters of the RFB system 100 such as flow speed of the anolyte and catholyte solutions through their respective chambers, operating temperature, etc.

In a charging mode of operation of the RFB system 100, the processes described above with respect to the discharge mode of operation are reversed. In the charging mode of operation, electrons flow from the catholyte chamber 114 by way of the cathode electrode 116 through an electrical power supply (e.g., connected to the cathode electrode 116 and the anode electrode 112 as is the load 104) and then to the anolyte chamber 110 by way of the anode electrode 112. To balance the flow of electrons from the catholyte chamber 114 to the anolyte chamber 110 and maintain charge neutrality in the chambers 110, 114, in the charging mode of operation of the RFB system 100 $Na^+$ ions migrate from the catholyte chamber 114 to the anolyte chamber 110 across the NaSICON barrier 118.

In either the discharge mode or the charging mode of operation of the RFB system 100, the pumps 124, 126 cycle the anolyte and catholyte solutions through their respective chambers 110, 114 and tanks 120, 122. A total energy storage capacity of the system 100 depends upon parameters of the system 100 such as an amount of charge-balancing $Na^+$ ions in the tanks 120, 122 and a total amount of the active redox species in the anolyte and catholyte solutions in the anolyte tank 120 and catholyte tank 122 respectively. As the active redox species are reduced or oxidized in the anolyte chamber 110 and catholyte chamber 114, the solutions are "refreshed" by fluid flow from the tanks 120, 122 with active redox species that have not yet been reduced or oxidized. A power output of the cell 102 is dependent on parameters of the cell 102 such as a thickness of the NaSICON barrier 118, and surface area of interfaces 128, 130 between the barrier 118 and the anolyte chamber 110 and catholyte chamber 114, respectively. Parameters affecting the energy capacity of the system 100 or the power output of the system 100 can be selected and designed for independently, such that the energy capacity and the power output need not be dependent upon one another.

The NaSICON barrier 118 separates the anolyte chamber 110 and the catholyte chamber 114 of the RFB system 100, and is configured to prevent transport of active redox species or solvent between the anolyte chamber 110 and the catholyte chamber 114. In exemplary embodiments, the NaSICON barrier 118 is a solid barrier (e.g., without holes disposed therein). NaSICON is a highly permeselective fully densified ceramic solid, such that substantially none of the active redox species or solvents in either the anolyte chamber 110 or the catholyte chamber 114 cross the barrier 118. For example, in experiments conducted with iron-based active redox species in aqueous solution in an anolyte chamber and a catholyte chamber, an upper limit of permeability of a NaSICON barrier to the anolyte and catholyte solutions was found to be $4 \times 10^{-10}$ cm$^2$/minute based upon measures of material composition performed by way of ultraviolet-visible spectroscopy and cyclic voltammetry techniques. This upper limit was determined based upon measurements using these techniques that detected no crossover of active redox species or solvents between the anolyte chamber and the catholyte chamber. As used herein with respect to the barrier 118, therefore, impermeable is defined as having a permeability of less than about $4 \times 10^{-10}$ cm$^2$/minute.

By contrast, Na$^+$ ions are freely conducted across the barrier 118. For example, at room temperature (e.g., a range of temperatures spanning at least between about 40 degrees Fahrenheit and about 100 degrees Fahrenheit), the NaSICON barrier 118 has an ionic conductivity of between about $10^{-3}$ S/cm and about 10'S/cm with respect to Na$^+$ ions. Thus, in contrast with conventional RFBs in which substantial crossover of active redox species and solvents occurs across a membrane that separates the anolyte chamber and the catholyte chamber, the RFB system 100 with the NaSICON barrier 118 maintains separation between the redox species and solvents in the anolyte chamber 110 and the redox species and solvents in the catholyte chamber 114.

Since the barrier 118 maintains separation between the anolyte solution in the anolyte chamber 110 and the catholyte solution in the catholyte chamber 114, in various embodiments the anolyte solution and the catholyte solution comprise different active redox species and/or different solvents. For example, the anolyte solution can comprise a first active redox species dissolved in a first solvent while the catholyte solution comprises a second active redox species dissolved in a second solvent. In another example, the anolyte solution and the catholyte solution can comprise the same solvent but different active redox species. In still another example, the anolyte solution can comprise the same active redox species as the catholyte solution, but a different solvent than the catholyte solution. For instance, in an exemplary embodiment the anolyte solution is an aqueous solution while the catholyte solution is a solution wherein the solvent is an alcohol, with the same active redox species dissolved in the anolyte solution and the catholyte solution. In other embodiments, the anolyte solution and the catholyte solution comprise same or different dissolved salts. For example, the anolyte solution may comprise sodium chloride while the catholyte solution comprises sodium sulfate. In still other examples, the anolyte solution and the catholyte solution may have a same or different pH.

The NaSICON barrier 118 is stable in the presence of water and so is compatible with aqueous anolyte and catholyte solutions. Using water as the solvent in the anolyte chamber 110 and/or the catholyte chamber 114 can reduce cost or increase safety of the system 100 as compared to more volatile or expensive solvents.

In exemplary embodiments, the anolyte and catholyte active redox species are metals, including iron, manganese, cobalt, titanium, and chromium. Complexing a metal active redox species with various ligands can increase solubility of the active redox species in a solvent at neutral pH and affect the redox potential of the active redox species, which in turn affects voltage of the cell 102. In various embodiments, a transition metal active redox species in either or both of the anolyte solution or the catholyte solution is complexed with ligands of ethylenediaminetetraacetic acid (EDTA), 1,10-phenanthroline, 2,2' bipyridyl (bpy), disodium 4,5-dihydroxy-1,3-benzenedisulfonic acid (Tiron), 1,3-dihydroxybenzene (catechol), chromotropic acid, or acetylacetonate to form the active redox species in either or both of the anolyte solution or the catholyte solution. In other embodiments, hexa-cyanide complexes of iron, manganese, cobalt, titanium, and chromium are used as the active redox species in either or both of the anolyte or catholyte solutions. Other active redox species are also contemplated, such as quinone and viologen.

The voltage of the cell 102 that is developed between its anode electrode 112 and its cathode electrode 116 is based in part upon the active redox species of the anolyte solution and the catholyte solution. The active redox species in either the anolyte or the catholyte solutions may be selected based upon a desired electric potential between the anode 106 and the cathode 108. For example, where the solvent in either the anolyte chamber 110 or the catholyte chamber 114 is water, the voltage between the electrodes 112, 116 of the cell 102 may be desirably limited to prevent the evolution of H$_2$ or O$_2$ gases in the cell 102. The active redox species in the anolyte solution and the catholyte solution may be selected to limit the voltage of the cell 102 to a voltage below an activation overpotential sufficient to cause evolution of H$_2$ or O$_2$ gases in the cell 102. In one exemplary embodiment, the anolyte solution comprises an aqueous solution of iron complexed with ligands of EDTA while the catholyte solution comprises an aqueous solution of iron complexed with ligands of bpy. In experiments, this configuration is found to yield a cell voltage of about 1.0 V under standard temperature and pressure conditions, which is sufficiently low to prevent formation of H$_2$ or O$_2$ gases in the aqueous anolyte and catholyte solutions. Other combinations of transition metal coordination centers and ligands described herein are contemplated as being suitable for inclusion in the anolyte solution or the catholyte solution in the RFB system 100.

Material compositions for the electrodes 112, 116 may vary based upon the makeup of the anolyte and catholyte solutions used in the system 100. In an example, it is desirable that the anode electrode 112 be substantially nonreactive to compounds making up the anolyte solution and that the cathode electrode 116 be substantially nonreactive to compounds making up the catholyte solution. In another example, it is desirable that the anode electrode 112 and the cathode electrode 116 be good conductors of electricity. In still further examples, it is desirable that the electrodes 112, 116 readily facilitate a redox reaction between the active redox species in the anolyte chamber 110 and the catholyte chamber 114. In exemplary embodiments, the electrodes 112, 116 are composed of platinum, gold, or various forms of carbon (e.g., graphite). In some embodiments, the anode electrode 112 and the cathode electrode 116 may be composed of different materials. By way of example, it may be desirable for the anode electrode 112 to be composed of platinum while graphite may be selected to make up the cathode electrode 116 if the catholyte solution comprises species that react with platinum.

Various geometric configurations of the cell 102 are contemplated as being within the scope of this disclosure. For example, the chambers 110, 114, the electrodes 112, 116, and the barrier 118 may be in the shape of prisms such that their respective interfaces have a polygonal shape. In other examples, the chambers 110, 114, the electrodes 112, 116, and the barrier 118 may have a cylindrical shape such that their respective interfaces define circles. Other geometric configurations are also contemplated.

Figure 2:
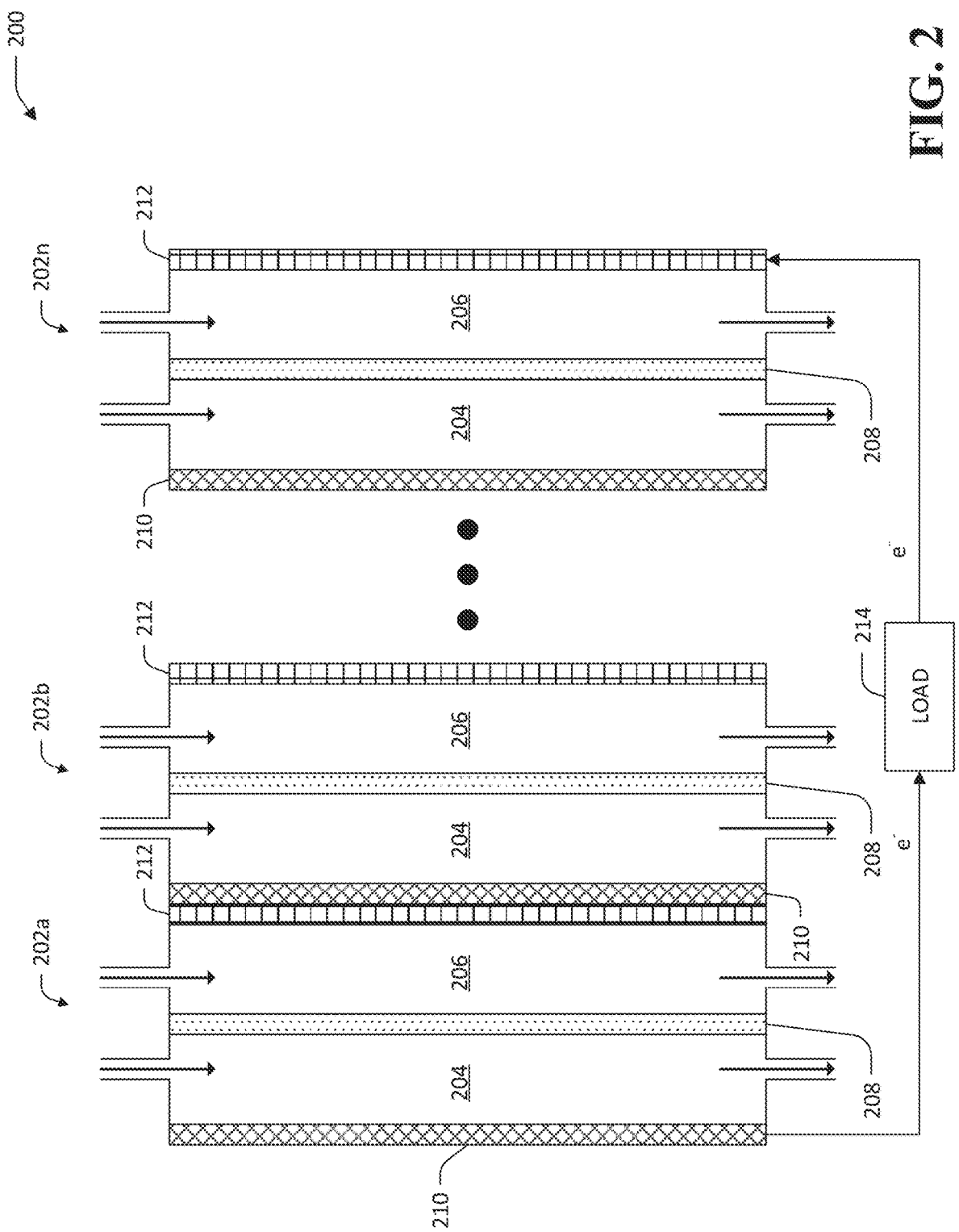
FIG. 2 is a diagram of an exemplary multi-cell configuration of a redox flow battery.

The exemplary cell 102 described above may be adapted to function as part of a multi-cell battery system in order to increase a total open-circuit voltage of the battery system. Referring now to FIG. 2, an exemplary multi-cell RFB battery system 200 is illustrated. The multi-cell system 200 includes a plurality of n RFB cells 202a-202n. Each of the cells 202a-202n comprises an anolyte chamber 204, a catholyte chamber 206, and a NaSICON barrier 208 that separates the anolyte chamber 204 and the catholyte chamber 206. Each of the cells 202a-202n further comprises an anode electrode 210 and a cathode electrode 212. The n cells 202a-202n are connected in series such that, except for terminal cells 202a and 202n that are adjacent to and connected to only one other cell, each of the cells in the cells 202a-202n (e.g., the cell 202b) is adjacent to and connected to two other cells. The non-terminal cells in the cells 202a-202n are each connected such that the anode electrode 210 of each non-terminal cell is connected to the cathode electrode 212 of a first adjacent cell in the cells 202a-202n, and the cathode electrode 212 of each non-terminal cell is connected to the anode electrode 210 of a second adjacent cell in the cells 202a-202n. Thus, for example, the anode electrode 210 of the cell 202b is connected to the cathode electrode 212 of the cell 202a, while the cathode electrode 212 of the cell 202b is connected to the anode electrode 210 of the second adjacent cell (not pictured) to 202b. In an exemplary embodiment, the electrodes 210, 212 form exterior walls of the cells 202a-202n, such that the cells 202a-202n are in electrical contact when their exterior walls make physical contact. This facilitates series connection, or stacking, of the cells 202a-202n to form a compact multi-cell battery system 200 without requiring complex or fragile wiring to make electrical connection between the cells 202a-202n.

A load 214 is connected to the terminal cells 202a and 202n. A first terminal of the load 214 is connected to the anode electrode 210 of the cell 202a while a second terminal of the load 214 is connected to the cathode electrode 212 of the cell 202n. By virtue of the series connection of the cells 202a-202n, a total voltage developed between the anode electrode 210 of the cell 202a and the cathode electrode 212 of the cell 202n is approximately the sum of voltages between the anode electrode 210 and cathode electrode 212 of each of the cells 202a-202n. Thus, for example, if each of the cells 202a-202n has an approximately equal voltage between its anode electrode 210 and its cathode electrode 212, the voltage at the load 214 would be approximately equal to Vn, where V is the voltage of an individual cell in the cells 202a-202n and n is the number of cells in the system 200. In other embodiments, a multi-cell battery system may include only two cells, e.g., the cells 202a and 202b.

Various configurations of anolyte and catholyte tanks (not shown) may be used to supply the RFB cells 202a-202n of the multi-cell RFB system 200. In one exemplary embodiment, a single anolyte tank supplies anolyte solution to the anolyte chamber 204 of each of the cells 202a-202n, and a single catholyte tank supplies catholyte solution to the catholyte chamber 206 of each of the cells 202a-202n. In another exemplary embodiment, each of the cells 202a-202n has its own respective anolyte and catholyte tanks. It is to be understood that various arrangements and combinations of devices and structures (e.g., pumps, pipes, gravity feed systems, etc.) may be used to facilitate fluid flow between anolyte and catholyte chambers of battery cells described herein, and their respective fluid supply tanks.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

All percentages and averages are by weight unless the context indicates otherwise. If not specified above, the properties mentioned herein may be determined by an applicable ASTM standard, or if an ASTM standard does not exist for the property, the most commonly used standard known by those of skill in the art may be used.

What is claimed is:

1. A redox flow battery, comprising:
   an anode portion comprising:
      an anolyte chamber having an anolyte solution flowing therethrough, the anolyte solution comprising:
         a first active redox species; and
         a first sodium salt; and
      an anode electrode;
   a cathode portion comprising:
      a catholyte chamber having a catholyte solution flowing therethrough, the catholyte solution comprising:
         a second active redox species; and
         a second sodium salt; and
      a cathode electrode; and
   a barrier that separates the anolyte chamber from the catholyte chamber, the barrier comprising a sodium-super-ionic-conductor (NaSICON), wherein responsive to an electrical load being connected to the anode electrode and the cathode electrode, sodium ions migrate from the anolyte solution to the catholyte solution across the NaSICON barrier to balance a flow of electrons from the anode electrode to the cathode electrode.

2. The redox flow battery of claim 1, wherein the first active redox species and the second active redox species are different species.

3. The redox flow battery of claim 1, wherein the first active redox species is dissolved in a first solvent and the second active redox species is dissolved in a second solvent that is different from the first solvent.

4. The redox flow battery of claim 3, wherein the first solvent includes water and the second solvent includes an alcohol.

5. The redox flow battery of claim 1, wherein the barrier is impermeable to the first active redox species and the second active redox species.

6. The redox flow battery of claim 1, wherein the barrier is configured to prevent transport of active redox species or solvent between the anolyte chamber and the catholyte chamber.

7. The redox flow battery of claim 1, wherein at least one of the anolyte solution or the catholyte solution comprises a metal complex.

8. The redox flow battery of claim 7, wherein the metal complex comprises a species selected from the group consisting of: iron, manganese, cobalt, titanium, and chromium.

9. The redox flow battery of claim 8, wherein the metal complex comprises a ligand selected from the group consisting of:
- ethylenediaminetetraacetic acid (EDTA);
- 1, 10 phenanthroline;
- 2, 2 bipyridyl;
- disodium 4,5-dihydroxy-1,3-benzenedisulfonic acid (Tiron);
- catechol;
- chromotropic acid;
- acetylacetonate; and
- cyanide.

10. The redox flow battery of claim 1, wherein at least one of the first sodium salt or the second sodium salt comprises sodium sulfate, sodium chloride, sodium bromide, or sodium phosphate.

11. The redox flow battery of claim 1, wherein at least one of the anolyte solution or the catholyte solution comprises at least one species selected from the group consisting of quinone and viologen.

12. The redox flow battery of claim 1, wherein the anolyte solution is an aqueous solution, wherein the first active redox species is a first transition metal complex that comprises a first transition metal and a first ligand, and the catholyte solution is an aqueous solution, wherein the second active redox species is second transition metal complex that comprises the first transition metal and a second ligand.

13. The redox flow battery of claim 12, wherein the first transition metal complex comprises a complex of iron and ethylenediaminetetraacetic acid (EDTA), and wherein the second transition metal complex comprises a complex of iron and 2,2 bipyridyl (bpy).

14. A battery system, comprising:
a plurality of battery cells connected in series, wherein each of the battery cells comprises:
an anolyte chamber having an anolyte solution flowing therethrough, the anolyte solution comprising:
an anolyte active redox species; and
a first sodium compound;
a catholyte chamber having a catholyte solution flowing therethrough, the catholyte solution comprising:
a catholyte active redox species; and
a second sodium compound; and
a sodium-super-ionic-conductor (NaSICON) barrier that separates the anolyte chamber from the catholyte chamber such that sodium ions migrate between the anolyte chamber and the catholyte chamber across the barrier responsive to redox reactions occurring in the anolyte chamber and the catholyte chamber.

15. The battery system of claim 14, wherein for each of the battery cells, the anolyte solution is a first aqueous solution of the anolyte active redox species, the catholyte solution is a second aqueous solution of the catholyte active redox species, wherein the anolyte active redox species comprises a first metal complex and the catholyte active redox species comprises a second metal complex.

16. The battery system of claim 14, wherein for each of the battery cells, the anolyte chamber contains a first solvent, the anolyte active redox species dissolved in the first solvent, the catholyte chamber contains a second solvent, the catholyte active redox species dissolved in the second solvent.

* * * * *